United States Patent [19]

Fisher et al.

[11] Patent Number: 4,495,799

[45] Date of Patent: Jan. 29, 1985

[54] DETERMINING THE LEVEL OF CONTAMINANTS IN A HYDRAULIC SYSTEM

[75] Inventors: Martin J. Fisher, Milton Keynes; Roger A. Heron, Stagsden; Martin L. Hughes, Newport Pagnell, all of England

[73] Assignee: National Research Development Corporation, London, England

[21] Appl. No.: 446,619

[22] Filed: Dec. 3, 1982

[30] Foreign Application Priority Data

Dec. 4, 1981 [GB] United Kingdom ................ 8136634

[51] Int. Cl.³ ............................................. G01N 15/06
[52] U.S. Cl. .................................................... 73/61 R
[58] Field of Search ................................ 73/61 R, 61.4

[56] References Cited

U.S. PATENT DOCUMENTS

| | | |
|---|---|---|
| 3,050,987 | 8/1962 | Osgood . |
| 3,182,670 | 5/1965 | Howell . |
| 3,359,786 | 12/1967 | Von Alfthan ...................... 73/61 R |
| 3,832,094 | 8/1974 | Raymond . |
| 3,941,958 | 3/1976 | Flesburg . |
| 3,952,580 | 4/1976 | Bennett ................................ 73/61.4 |

FOREIGN PATENT DOCUMENTS 1098186 1/1968 United Kingdom .
1428602 3/1976 United Kingdom .

*Primary Examiner*—Gerald Goldberg
*Assistant Examiner*—Joseph W. Roskos
*Attorney, Agent, or Firm*—Cushman, Darby & Cushman

[57] ABSTRACT

A device for determining the level of particulate contamination in a hydraulic system. Between the inlet and outlet of the device the fluid passes through the narrow clearance between a piston and a surrounding bore. As the clearance becomes obstructed by contaminant, pressure rises in a chamber upstream of the piston. Rise of this pressure above a certain level is detected by a detector which both triggers a counter and operates a solenoid to withdraw the piston and release trapped contaminant, after which the piston returns and another cycle of contaminant build-up begins. The frequency of the release of the piston indicates the degree of contamination of the fluid. Instead of pressure build-up, parameters related to fluid flow may be used to trigger the counter and the release of contaminants from clearance, and means may be provided to meter individual, fixed-volume charges from the general body of fluid and discharge them through a clearance. The clearance may as an alternative be arranged to be cleared by back flushing.

18 Claims, 9 Drawing Figures

DETERMINING THE LEVEL OF CONTAMINANTS IN A HYDRAULIC SYSTEM

The present invention relates to determining the level of particulate contaminant in a hydraulic system.

The presence of particulate contamination in the hydraulic fluid of a hydraulic system is inevitable. It is known that such contamination plays a significant role in the reliability and service life of the hydraulic system, and that severe cases of contamination may cause accelerated wear of hydraulic system components of catastrophic failure of the system. The amount of solid contaminant in a hydraulic system will, by wear on moving parts of the system and by activities such as 'topping up' of system fluid, tend to increase during use of the system. At some stage in the life of the system the amount of contaminant may exceed that which is deemed acceptable indicating that items such as fluid filters or the fluid itself may require renewal. The acceptable amount of contaminant will vary with design and usage of the system.

It is therefore desirable that a hydraulic system should contain some device capable of detecting solid contaminant present in the system, and it is further desirable that such a device should be of a form such that it is suitable for permanent installation in the hydraulic system.

According to the invention a device for determining the level of particulate contamination in a hydraulic system comprises inlet means for hydraulic fluid, outlet means for hydraulic fluid, releasable and restorable means for collecting particulate contaminants in hydraulic fluid flow between the inlet means and outlet means, detecting means for detecting particulate contaminant obstruction at the releasable collecting means above a predetermined level, and means responsive to said detecting means for recording the occurrence of this level of obstruction, for releasing the collected contaminants from said collecting means and for restoring the collecting means to their unobstructed state. The releasable collecting means may comprise a clearance for hydraulic flow between said inlet and outlet means, dimensioned to effect entrapment of particulate contaminant in the hydraulic fluid and so become obstructed. The clearance may be formed between two relatively-moving components, such relative movement being used to effect the release of said collected contaminants. The two components may be a piston of circular section movable within a bore of similar section, and separated from it by an annular clearance, and the releasable collecting means may be connected to the outlet means so as to release collected contaminants to those outlet means.

The detecting means may comprise a diaphragm, one side of which is in communication with said inlet means through a flow restrictor for inducing a reduced pressure of inlet hydraulic fluid at said one side, and with said outlet means through said releasable collecting means, said diaphragm being deflectable from a normal rest position in response to pressure rise in the hydraulic fluid at said one side due to build-up of contaminant at said collecting means, and means for recording a predetermined amount of deflection of said diaphragm. The flow restrictor may be of simple sharp-edged orifice or like type which tends not to entrap particulate contaminant within it. The recording means may comprise a normally open switch and an indexing counter, said switch being closable by said diaphragm after deflection by said predetermined amount, to thereby index said counter, and the switch may be electrical and actuable by contact during movement of the diaphragm by a magnetic bar attached to the diaphragm, a spring being positioned between the diaphragm and the switch to maintain the bar at a spacing from the switch.

The switch may be coupled to a magnetic coil arranged to move one of the two relatively-movable components from its normal rest position upon energisation of the coil when the switch is closed, whereby to release build-up of particulate contaminant at the collecting means for delivery to the outlet means. That component may be biased to its rest position by a spring for resisting said pressure rise at said one side of the diaphragm, and yielding to a pressure rise at said one side due to return movement of the diaphragm after deflection to its normal rest position, whereby to move the component and release comtaminant at said clearance.

The recording means may comprise a piston movable in a bore between a normally held stationary position and a forward position in response to deflection of the diaphragm, the bore being open to the other side of said diaphragm, and counter means for indexation by said piston in its forward position. The bore of said piston may have a first inlet for delivery of hydraulic fluid at inlet pressure thereto, to constrain said piston to said stationary position, and the diaphragm may have a plunger slidable within said piston, and a spring between the diaphragm and said piston, said spring being compressible upon deflection of the diaphragm to move the plunger within the piston until sufficient force is built-up in the spring to move said piston to its forward position. The bore of said piston may also have a second inlet for delivery of fluid at inlet pressure to the other side of said diaphragm, and a channel communicating between said other side and said outlet means, said second inlet being closed by said piston in its stationary position and opened in its forward position, whereby the diaphragm is returned to it original position by hydraulic fluid at inlet pressure entering said other side through said second inlet.

The detecting means may alternatively comprise a fluid flow detecting device connected between said collecting means and said outlet means, and a restrictor positioned in the fluid passage between said fluid flow detection device and said collection means, said fluid flow detection device thus being capable of detecting the alteration in fluid flow rate and fluid volume passing through said collecting means as they become blocked with contaminant. In a device also including a monitoring device and an indexing counter, the fluid flow detecting device may pass an electrical signal to the monitoring device which may send an actuating signal to the indexing counter when the electrical signal from the fluid flow detecting device satisfies a predetermined set of criteria. The device may also include a magnetic coil arranged when energised to release the collecting means, and the monitoring device may send an energising signal to the magnetic coil.

An alternative passage may be provided for fluid between the collecting means and the outlet means so as to by-pass the fluid flow detection device, and there may be means to open this passage to the fluid when there is risk of excessive flow rate through the fluid flow detection device.

There may also be a metering device located between the inlet means and the releasable collecting means, so that the metering device may receive a known and finite volume of hydraulic fluid from the inlet means and then discharge that volume through the collecting means.

The invention also includes a method of determining the level of particulate contaminant in a hydraulic system comprising collecting particulate contaminant in hydraulic fluid flow in the system, releasing the collected contaminant in response to having collected more than a predetermined quantity of a particulate contaminant, and determining said level by reference to the frequency of release. The particulate contaminant may be released after detection of a rise in the pressure of fluid flow due to the collection of particulate contaminant, or after detection of a reduction in the level of fluid flow due to that collection, or after the total volume of fluid passing through the point of collection has reached a predetermined value.

The invention will now be described, by way of example, with reference to the accompanying drawings in which.

Figure 1:
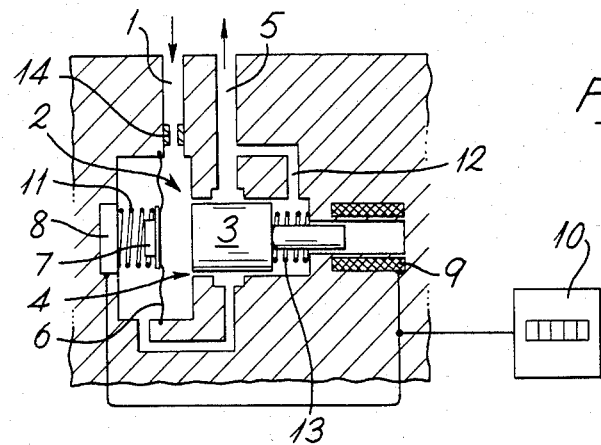
FIG. 1 is a schematic diagram showing a section through a device according to one embodiment of the invention.

The device of FIG. 1 comprises a piston 3 and diaphragm 6 fitted into a stepped chamber 2 fed by an inlet channel 1 for hydraulic fluid. Channel 1 is fitted with a flow restrictor 14, of sharp-endged orifice or other type which does not tend to accumulate contaminant from the fluid passing through it and so in time to become blocked. The diaphragm carries a magnetic or ferrous bar 7 and a spring 11 in a cavity. A magnetic or proximity switch 8 is positioned adjacent to the bar 7 and connected electrically to both a coil 9 and an electrical counter 10. The coil 9 is positioned so as to act upon the piston 3. The piston carries a spring 13 as shown in the Figure. The diameters of the piston 3 and the bore around it are such that a small clearance 4 exists between them. The critical dimensions of the clearance 4 will be typically within range $5 \times 10^{-6}$m to $1 \times 10^{-4}$m. Fluid passing through the clearance 4 is conducted away by outlet channels 5 and 12.

In operation, a proportion of system fluid containing solid contaminant enters the device through channel 1, and passes through the restrictor 14 and the clearance 4 into the outlet channel 5. Some solid particles are deposited in the clearance 4, thereby restricting the flow and raising the pressure in chamber 2. As particle accumulation continues, the pressure in chamber 2 forces the diaphragm 6 away from the piston 3, thus compressing spring 11. The spring 13 is such that the piston 3 experiences no substantial movement during this stage. At a predetermined deflection of the diaphragm 6, however, the bar 7 will cause the switch 8 to close, thereby activating the coil 9 and indexing the counter 10. The coil 9 pulls the piston 3 away from the diaphragm, compressing spring 13 and releasing contaminant trapped in the clearance 4 into the outlet channel 5. Fluid trapped behind the piston 3 may escape via channel 12 to outlet. This movement of the piston 3 causes the pressure in chamber 2 to fall thus allowing the diaphragm 6 to return to its original position. This causes the switch 8 to open, switching off coil 9 and releasing the piston 3. The device has now returned to its original state and the cycle may begin again.

The alternative embodiment of the invention shown in FIG. 2 again comprises an inlet channel 1 connecting through a restrictor 14 to a chamber 2 containing a piston 3 and diaphragm 6, a clearance 4 between the piston 3 and its bore allowing fluid to pass to an outlet channel 5, and a channel 12 communicating between the outlet 5 and the back of the piston 3. Piston 3 is again acted on by a spring 13. In this embodiment however a further channel fitted with an orifice 15 communicates between the outlet 5 and the back of the diaphragm 6, and the diaphragm 6 carries both a rod 17 and the spring 11, and a piston 19 is free to slide over a limited distance on rod 17 and is acted on by spring 11. The piston 19 carries at one end a rod fitted with a magnet 20, this magnet acts upon a magnetically operated counter 10, and passages 16 and 18 communicate between the bore of the piston 19 and the inlet passage 1.

Figure 2:
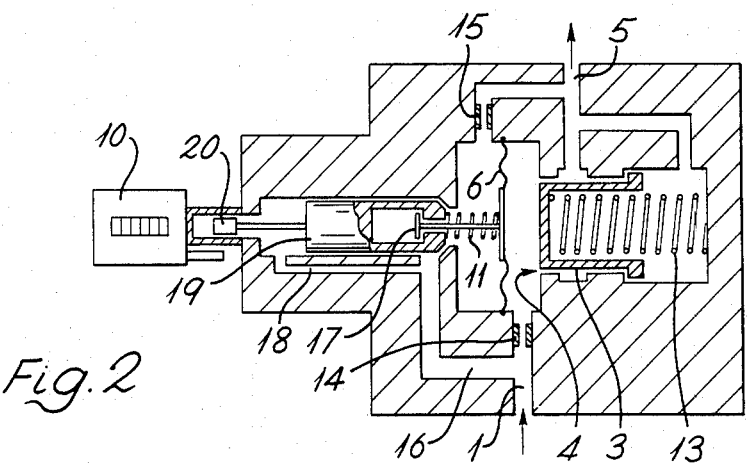
FIGS. 2 to 5 are schematic diagrams each showing a section through a device according to a different further embodiment of the invention.

In operation of the embodiment of the invention shown in FIG. 2 a proportion of the hydraulic system fluid containing solid contaminant enters via channel 1 and passes through the orifice 14 into the chamber 2. Restrictor 14 produces a drop in fluid pressure between channel 1 and chamber 2. Fluid passes from chamber 2 via the clearance 4 to the outlet channel 5. Solid contaminant particles are trapped by the clearance 4, restricting the flow and causing a pressure rise in chamber 2. As particle accumulation continues, the consequent rise of pressure in chamber 2 forces the diaphragm 6 away from piston 3 and towards piston 19, thereby compressing spring 11. Piston 3 is restrained from movement by spring 13, and piston 19 is restrained from movement by the effect of fluid pressure communicated via channel 18.

At a predetermined deflection of diaphragm 6, the force developed in spring 11 is sufficient to overcome the aforementioned restraint on piston 19, and the piston moves away from the diaphragm. Movement of the piston 19 causes the magnet 20 to approach and index the counter 10, and in addition permits fluid at the pressure of the inlet channel 1 to communicate via channel 16 with the back of diaphragm 6. The presence of fluid at inlet pressure behind diaphragm 6 causes the diaphragm to move towards piston 3, creating a pressure rise in chamber 2 sufficient to move piston 3 away from chamber 2, thereby compressing spring 13. Contaminant particles present in clearance 4 are now released to the outlet channel 5, and the movement of the diaphragm 6 causes piston 19 to be returned to it original position thus shutting off high pressure fluid from the back of the diaphragm. Fluid behind the diaphragm returns to outlet line pressure by communication via orifice 15, and movement of the piston 3 results in a drop of pressure in chamber 2, allowing both piston 3 and diaphragm 6 to return to their original positions. The device has now returned to its original state and the cycle may begin again.

Figure 3:
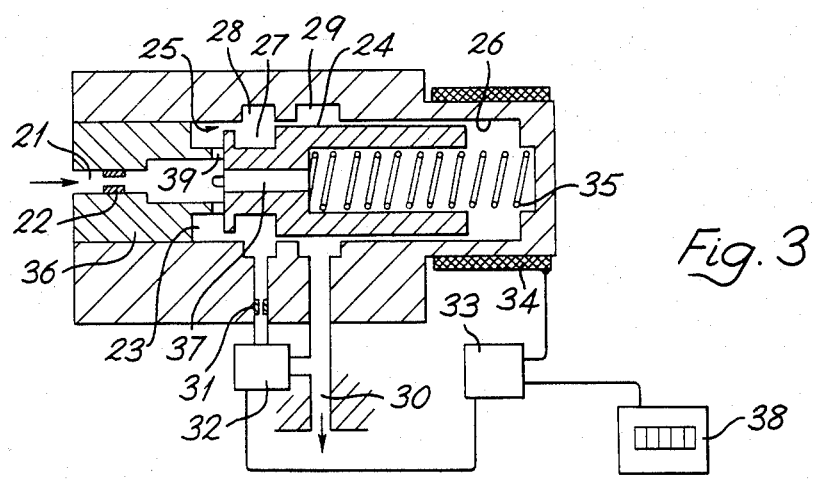

The further embodiment of the invention shown in FIG. 3 employs means for detecting the flow of fluid through the clearance. In this embodiment, a piston 24 is free to move in a close fitting bore 26. At one end of the piston its diameter is slightly reduced in order to provide an annular clearance 25 which communicates between a chamber 23 and an annular chamber 27 formed in piston 24. Further annular chambers 28 and 29 are formed in the bore 26. Chamber 23 communicates with a fluid inlet channel 21 via a restrictor 22, and chamber 28 communicates with a fluid outlet channel 30 via a restrictor 31 and a flow detection device 32. Chamber 29 communicates directly with outlet passage 30. Electrical signals from the flow detection device 32 are passed to an electronic monitoring device 33. This in turn passes electromagnetic signals to a coil 34 which can act on piston 24, and to an electrical counter 38. A spring 35 acts on piston 24 to hold it against a stop 36, and the strength of spring 35 is such that it may be overcome by the action of coil 34. Holes 39 and passage 37 allow free access for the fluid in chamber 23 to both sides of piston 24.

In operation of the embodiment of the invention shown in FIG. 3, fluid and contaminants enter chamber 23 by means of inlet passage 21 and restrictor 22. The pressure in chamber 23 causes fluid to flow through the annular clearance 25 into chambers 27 and 28, and thence to flow detection device 32. The dimensions of clearance 25 are such that some or all of the contaminant in the fluid becomes trapped in the clearance, partially blocking it and reducing the rate of fluid flow. After passing through the flow detection device 32, fluid passes to the outlet passage 30.

The electrical signals from the flow detection device 32 are monitored by the electronic monitoring device 33, which detects the reduction in fluid flow rate through device 32 as clearance 25 becomes blocked and compares this with a predetermined set of criteria for fluid flow rate and total volume flow through the device 32. When the criteria are satisfied by the incoming signal, monitoring device 33 passes an electrical signal to counter 38, which then indexes one unit. At the same time an electromagnetic signal is passed to coil 34 which energises and pulls piston 24 away from stop 36. Withdrawal of piston 24 from stop 36 allows the contaminant trapped in clearance 25 to be washed into chambers 27 and 28. In the withdrawn position of piston 24, chamber 27 connects together annular chambers 28 and 29. Fluid entering chamber 27 will then, by preference, tend to flow directly via chamber 29 to outlet passage 30, because of the resistance to flow offered by restrictor 31 and flow detection device 32. In this way the flow detection device is protected from damage by excessive flow rates. After a short period of time, monitoring device 33 switches off coil 34, and thus releases piston 24 which returns to rest against stop 36 under the action of spring 35. The device has now returned to its original condition and the cycle may begin again.

If inlet conditions to the devices shown in FIGS. 1, 2 and 3 remain substantially constant, then each cycle performed by either represents the accumulation within, or passing through, the device of a substantially fixed amound of solid contaminant. It is thus evident that the rate of cycling, or the number of cycles performed in a fixed time period by either device may be used as a measure of the level of solid contaminant within the hydraulic system to which the device is attached. The embodiments of the invention shown in FIGS. 2 and 3 are better suited than that of FIG. 1 for use with systems required to operate in explosive or otherwise hazardous environments because they require no switch or other spark-generating device to be located close to the hydraulic fluid.

In the embodiments of the invention described so far with reference to FIGS. 1 to 3 of the drawings the releasable collecting means for contaminants have had the preferred form of a clearance between two relatively-movable components, such movement being used to release accumulated contaminants. In the further embodiment of the invention shown in FIG. 4 the alternative principle of the reversal of fluid flow through a number of fixed orifices is employed as a method of removal of accumulated deposits of contaminant in those orifices. An inlet channel 40 communicates with two spools 41, and 42 each free to move in its respective parallel bore. Each spool carries a rod 49, 50 passing through a seal 53, 51 and interconnected by means of an interlock pin 52. The interlock pin 52 may slide at right angles to the axes of the spools 41 and 42 and engages with suitable cut-outs in the rods 49 and 50. Movement of either spool along its axis may only occur when the other spool is effectively prevented from movement by the engagement of the interlock pin 52 with a cut-out in the rods 49 or 50, and rod 50 is arranged so as to operate a mechanical counter 54.

A plate 57, perforated with a number of suitably sized orifices for collecting particulate contaminant, communicates via channels 43 and 44 with two ports on the spool 42. Two further channels 47 and 48 communicate between the plate 57 and either end of the spool 41. Flow restrictions 55 and 56 are fitted into channels 47 and 48, channels 45 and 46 communicate between the ends of spool 42 and two ports on spool 41, and outlet ports 58 communicate with both spool 41 and spool 42.

Figure 4:
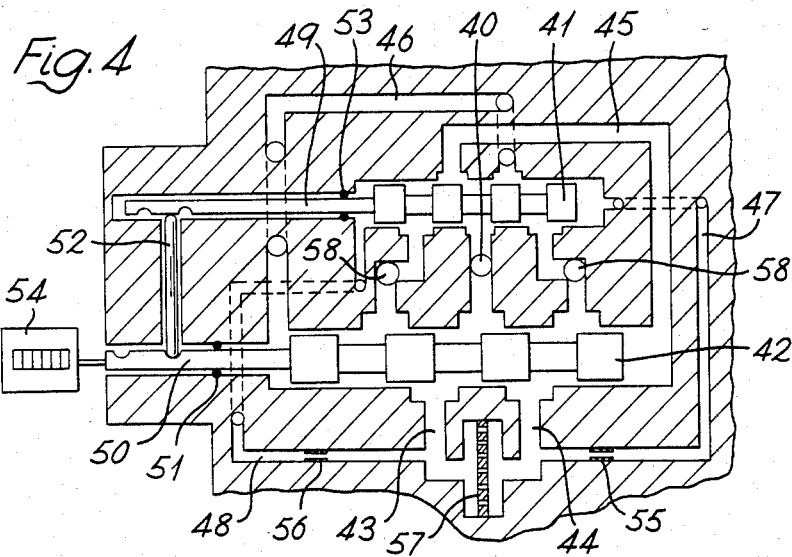

The method of operation of the embodiment of the invention shown in FIG. 4 is as follows, the terms of "right hand" and "left hand" referring to the figure as drawn.

Fluid containing solid contaminant particles passes from the inlet channel 40 via spool 42 and channel 43 to the orifice plate 57. Fluid at inlet pressure may also communicate via spool 41 with the right hand end of spool 42, thus forcing spool 42 to the left hand end of its bore. As fluid passes through plate 57, more of the solid contaminant particles in the fluid are deposited, thereby partially blocking the orifices in the plate. Fluid then passes via channel 44 and spool 42 to an outlet port 58. Fluid at outlet pressure is also admitted via spool 41 to the left hand end of spool 42. As deposition of particles at plate 57 continues the pressure difference between channels 47 and 48 will increase, and a nett flow of fluid into channel 48 will cause the spool 41 to be displaced towards the right hand end of its bore, allowing fluid at inlet pressure to communicate via channel 46 with the left hand end of spool 42. Fluid at the right hand end of spool 42 falls to outlet pressure by communication via channel 45 with an outlet port 58.

The aforementioned changes result in a force on spool 42 to the right. However, the interlock pin 42 effectively prevents movement of spool 42 until spool 41 has been driven to the extreme right hand end of it bore. As spool 41 reaches the extreme right hand position the interlock pin 52 engages with a cut-out in rod 49 and releases rod 50 and spool 42. Spool 42 now moves to the extreme right hand end of its bore, indexing the counter 54, movement of spool 41 being prevented during movement of spool 42 by the interlock pin 52. Fluid from the inlet channel 40 may now flow via spool 42 and channel 44 to orifice plate 57, and from thence via channel 43 and spool 42 to an outlet port 58. The direction of fluid flow through the orifice plate 57 is thus in the opposite direction to that heretofore described, so tending to release accumulated contaminant deposits from the plate and discharge them to outlet port 58.

As fluid continues to pass through orifice plate 57 in the new direction some contaminant particles in the fluid are deposited on the face of the plate opposite to that on which they previously accumulated, thereby restricting the flow. As these new accumulations increase the pressure difference between channels 47 and 48 will increase, and a nett flow of fluid into channel 47 will cause the spool 41 to be displaced towards the left hand end of its bore. This displacement of spool 41 causes fluid at inlet pressure to communicate via channel 45 with the right hand end of spool 42, whilst fluid at the left hand end of spool 42 falls to outlet pressure by communication via channel 46 and spool 41 with an outlet port 58. A force to the left on spool 42 is the result. Movement of spool 42 is however prevented by the action of interlock pin 52 engaging in a cut-out in rod 50.

When spool 41 reaches the extreme left hand end of its bore, rod 50 and spool 42 are released by the interlock pin 52 and travel to the left hand end of the bore, movement of spool 41 being prevented by the interlock pin 52 whilst spool 42 is in motion. The device has now returned to it original state and the cycle may begin again.

Figure 5:
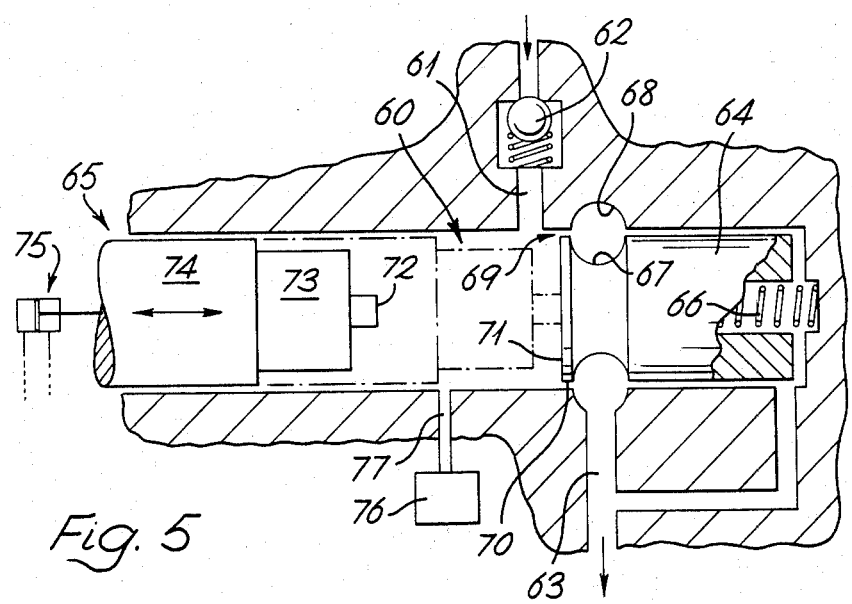

The further embodiment of the invention shown in FIG. 5 makes special use of a feature already referred to with reference to FIGS. 1 to 3, and which we have found to be characteristic of many hydraulic flow systems in which the typical contaminant particles are of metal or other very hard materials. This feature is that the accumulation of contaminant at a clearance, and thus the rate of increase of resistance at that clearance, tends to vary directly as the mass of contaminant reaching the clearance in unit time. Where this feature is present, therefore, an alternative is possible to those embodiments of the invention which have been shown in FIGS. 1 to 4 and in which it is the natural flow of fluid within the hydraulic circuit that causes contaminant to accumulate in the clearance, causing resistance of the clearance to rise. The alternative that now becomes possible is to draw off a known volume of fluid from the system as often as is desired, and then expel that volume to outlet at a chosen and constant flow rate through a clearance the dimensions and resistance of which are known when the expulsion begins. The dimensions are chosen so that if contamination exceeds a certain level, the resistance of the flow of the clearance rises to exceed a certain value before the expulsion stroke is finished, so causing the pressure of that part of the drawn sample remaining in the chamber to reach a value which cause a record to be made and/or a signal to be emitted indicating that level of contamination. Such an alternative version of the invention is illustrated in FIG. 5, in which fluid from a hydraulic system enters a metering device by way of an inlet channel 61 containing a non-return valve 62, and leaves it by way of an outlet channel 63 communicating with the return side of the hydraulic system (not shown). The metering device comprises a chamber 60 containing two pistons 64, 65. Piston 64 is mounted on a spring 66, a groove 67 in the side wall of the piston registers with a groove 68 in the side wall of chamber 60 and a clearance 69 is formed between the chamber wall and the short length 70 of the wall of piston 64 lying between groove 67 and an end face 71.

Piston 65 comprises a tip member 72, a forward part 73 which is of smaller diameter than chamber 60, and a more rearward part 74 of larger diameter which makes a close sliding fit within chamber 60, and piston 65 as a whole is reciprocated within chamber 60 by a motor indicated diagrammatically at 75. A pressure-sensitive switch 76 is connected to chamber 60 by a conduit 77.

One cycle of operation of the device begins with piston 64 in its rest position, as shown, but with piston 65 to the far right hand end of its travel in which tip 72 just touches face 71. Motor 75 now withdraws piston 65 to the other end of its stroke (as shown in FIG. 5) and in so doing opens valve 62 and draws in a charge of fluid of known volume from the hydraulic system through inlet 61. Piston 65 then reverses direction and is moved towards piston 64 at constant speed, so that valve 62 closes and fluid is expelled at constant flow rate through clearance 69 into the space bounded by registering grooves 67 and 68, and so to outlet 63. As this expulsion takes place the pressure of the fluid within chamber 60 will be proportional to the resistance offered by clearance 69, and the value of this resistance will rise as contaminant particles become lodged in the clearance. Switch 76 could be set, for instance, to be operated by the pressure which will exist within chamber 60 when the tip 72 of piston 65 meets face 71, and when the level of contaminant within the fluid is just above what is acceptable.

After tip 72 has contacted face 71, piston 65 continues to move to the right for a short distance, moving piston 64 with it against the force of spring 66 so that wall 70 moves into register with groove 68 and clearance 69 therefore widens. The fluid force holding valve 62 closed is therefore released, so that fluid flows from inlet 61 to outlet 63 under the normal pressure difference of the hydraulic system, flushing away to the outlet the contaminant particles that had lodged within clearance 69 as chamber 60 was exhausted. The cycle is now ready to be repeated. As will be appreciated, in this embodiment of the invention the piston-and-cylinder combination 60, 65 acts essentially as a device by which metered quantities of the hydraulic fluid may be tested for contamination in batch fashion, the time for each test depending primarily upon the chosen cycling speed of piston 65 rather than (as in embodiments previously described) upon the resistance of the device itself and the pressure difference across that part of hydraulic circuit within which the device is located.

Figure 6:
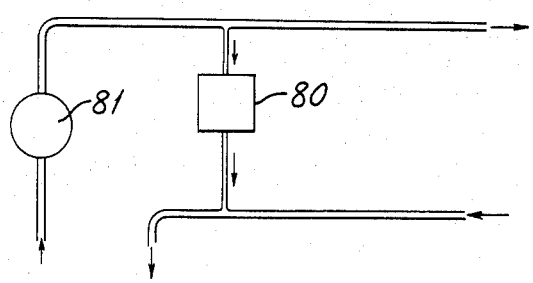
FIG. 6 is a schematic diagram showing a typical positioning of the device of the invention within a hydraulic circuit.

As shown in FIG. 6, the devices (referrenced 80) of FIGS. 1 to 5 may be connected between a hydraulic line carrying full system pressure and, commonly, the majority of fluid flow, and a line carrying the pressure at which fluid returns to the system sump, tank or pump 81 inlet.

Figure 7:
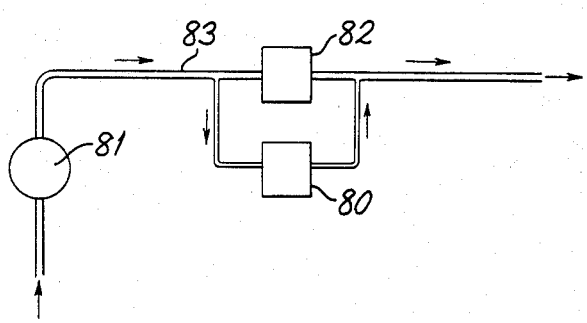
FIG. 7 is a schematic diagram showing an alternative positioning of the device of the invention in a hydraulic circuit.

As shown in FIG. 7, the devices 80 of FIGS. 1 to 5 may, as an alternative arrangement, be connected to any suitable high power hydraulic line 83 in parallel with a variable orifice 82, such that the inlet to the device is upstream of the variable orifice and the outlet from the device is downstream of the variable orifice.

Figure 8:
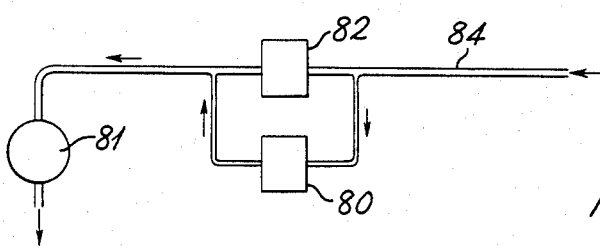
FIG. 8 is a schedule diagram showing a further alternative positioning to the device of the invention in a hydraulic circuit.

As shown in FIG. 8, the devices 80 of FIGS. 1 to 5 may, as a further alternative arrangement, be connected across a variable orifice 82 placed in the low pressure return line 84 of a hydraulic system, such that the inlet to the device is upstream of the variable orifice and the outlet from the device is downstream of the variable orifice.

Figure 9:
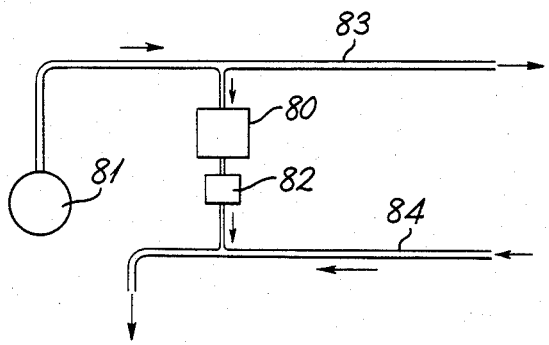
FIG. 9 is a schematic diagram showing a yet further alternative positioning of the device of the invention in a hydraulic circuit.

As shown in FIG. 9, the devices 80 of FIGS. 1 to 5 may, as yet a further alternative arrangement, be connected to a variable orifice 82 such that the outlet of the device is connected to the inlet of the variable orifice, the inlet of the device 80 being connected to the high pressure supply line 83 of the hydraulic system and the outlet of the variable orifice 82 being connected to the low pressure return line 84 of the hydraulic system.

We claim:

1. A device for determining the level of particulate contamination in a hydraulic system, comprising:
   inlet means for hydraulic fluid;
   outlet means for hydraulic fluid;
   releasable and restorable collecting means for collecting particulate contaminants in hydraulic fluid flow between said inlet means and said outlet means, said collecting means comprising first and second components capable of relative movement and defining between them a clearance for said hydraulic fluid flow, said clearance being dimensioned to effect entrapment of said particulate contaminants and so become obstructed, said two components being a piston of circular section movable within a bore of similar section, said piston and said bore being separated by an annular gap which constitutes said clearance, and said relative movement being usable to effect said release of said collected particulate contaminants;
   detecting means for detecting particulate contaminant obstruction at said collecting means above a predetermined level, and
   means responsive to said detecting means for recording the occurrence of said level of obstruction, for releasing the said collected contaminants from said collecting means, and for restoring said collecting means to their unobstructed state.

2. A device for determining the level of particulate contamination in a hydraulic system, comprising:
   inlet means for hydraulic fluid;
   outlet means for hydraulic fluid;
   releasable and restorable collecting means for collecting particulate contaminants in hydraulic fluid flow between said inlet means and said outlet means, said collecting means comprising first and second components capable of relative movement in the direction definable by a first axis, said first and second components presenting first and second surfaces respectively, said surfaces both being axisymmetric relative to said first axis and in use defining between them a clearance through which said hydraulic fluid flow passes, said clearance having a constant transverse dimension over a finite length relative to the direction of said hydraulic fluid flow through it;
   detecting means for detecting particulate contaminant obstruction at said clearance above a predetermined level, and
   means responsive to said detecting means for recording the occurrence of said level of obstruction, for relatively moving said first and second components to open said clearance and to release said collected contaminants from it, and for restoring said collecting means to their unobstructed state.

3. A device as claimed in claim 2 in which said collecting means are connected to said outlet means so that said collected contaminants when released pass to said outlet means.

4. A device as claimed in claim 2 including a flow restrictor and in which said detecting means comprises a diaphragm having first and second sides, means including said flow restrictor for establishing fluid communication between said first side of said diaphragm and said inlet means whereby a reduced pressure of said hydraulic fluid is induced against said first side of said diaphragm, and means including said collecting means for also establishing fluid communication between said first side of said diaphragm and said outlet means, said diaphragm being deflectable from a normal rest position in response to pressure rise in said hydraulic fluid against said first side due to said contaminant obstruction of said collecting means, and means for recording a predetermined amount of said deflection of said diaphragm.

5. A device as claimed in claim 4 in which said flow restrictor is of simple sharp-edged orifice or like type which tends not to entrap particulate contaminants within it.

6. A device as claimed in claim 4 wherein said recording means comprises a normally open switch and an indexing counter, said switch being closable by said diaphragm once deflected by said predetermined amount, whereby to index said indexing counter.

7. A device as claimed in claim 6 including a magnetic bar attached to said diaphragm, and a spring, wherein said switch is electrical and contact-actuable by said magnetic bar during movement of said diaphragm, said spring being positioned between said diaphragm and said switch so as normally to maintain said bar spaced apart from said switch.

8. A device as claimed in claim 6 including a magnetic coil coupled to said switch, said coil being arranged to move a first of said two relatively-movable components from its normal rest position when said coil is energised by the closing of said switch, whereby to release the collected contaminants from said collecting means.

9. A device as claimed in claim 8 wherein said first component is biased to its said normal rest position by a spring means, said spring means operating to resist said pressure rise occurring against said first side of said diaphragm as said diaphragm deflects, but operating so as to allow said first component to yield to the pressure existing against said first side of said diaphragm as said diaphragm returns to its rest position after deflection, whereby said first component moves and said contaminant is released from said clearance.

10. A device as claimed in claim 9 wherein said recording means also comprises a piston movable in a bore, said piston having a normally held stationary position and a forward position to which it moves in response to said deflection of said diaphragm, said bore being open to said second side of said diaphragm, said indexing counter being indexed, by said piston when in its said forward position.

11. A device as claimed in claim 10 wherein the said bore of said piston has a first inlet connected to said hydraulic fluid at the pressure existing at said inlet means, said fluid at said pressure acting upon said piston to constrain said piston to its said normally held stationary position.

12. A device as claimed in claim 11 wherein said diaphragm has a plunger slideable within said piston and a spring between said diaphragm and said piston, said spring being compressible upon deflection of said diaphragm to move said plunger within said piston until sufficient force is built up in said spring to move said piston to its said forward position.

13. A device as claimed in claim 12 wherein said bore of said piston has a second inlet connecting said second side of said diaphragm to fluid at the pressure existing at said inlet means, and a channel communicating said second side of said diaphragm with said outlet means, said inlet being closed by said piston when in its said normally held stationary position and opened when in its said forward position, whereby said diaphragm is returned to its said normal rest position by said hydraulic fluid at said inlet pressure reaching said second side of said diaphragm through said second inlet.

14. A device as claimed in claim 2 wherein said detecting means comprises a fluid flow detection device connected between said collecting means and said outlet means, and a restrictor positioned between said fluid flow detection device and said collection means, said fluid flow detection device being adapted to detect alteration in the rate of flow of said hydraulic fluid through said collecting means as said means become blocked with said particulate contaminants.

15. A device as claimed in claim 14 including a monitoring device and an indexing counter, and wherein said fluid flow detection device passes an electrical signal to said monitoring device which sends an actuating signal to said indexing counter when said electrical signal from said fluid flow detection device satisfies a predetermined criterion.

16. A device as claimed in claim 15 including a magnetic coil arranged when energised to release said collecting means, and in which said monitoring device is also adapted to send an energising signal to said magnetic coil.

17. A device as claimed in claim 14 wherein an alternative passage is provided for flow of said hydraulic fluid between said collecting means and said outlet means so as to by-pass said fluid flow detection device and wherein there are opening means to open said alternative passage to said fluid when there is risk of excessive flow rate through said fluid flow detection device.

18. A device as claimed in claim 2 including a metering device located between said inlet means and said releasable collecting means, said metering device being adapted to receive a predetermined volume of said hydraulic fluid from said inlet means and then to discharge said volume through said collecting means.

* * * * *